United States Patent [19]
Engelmann et al.

[11] Patent Number: 5,987,345
[45] Date of Patent: *Nov. 16, 1999

[54] METHOD AND SYSTEM FOR DISPLAYING MEDICAL IMAGES

[75] Inventors: Roger Engelmann, Chicago; Kenneth R. Hoffmann, Matteson; Heber MacMahon, Chicago; Kunio Doi, Willowbrook, all of Ill.

[73] Assignee: Arch Development Corporation, Chicago, Ill.

[*] Notice: This patent issued on a continued prosecution application filed under 37 CFR 1.53(d), and is subject to the twenty year patent term provisions of 35 U.S.C. 154(a)(2).

[21] Appl. No.: 08/757,611

[22] Filed: Nov. 29, 1996

[51] Int. Cl.[6] ................. A61B 5/00; G06K 9/00
[52] U.S. Cl. ............... 600/407; 128/920; 382/130; 345/116
[58] Field of Search ............... 600/407; 128/920, 128/922; 382/128, 130, 132, 305, 306, 307; 378/98, 62; 345/23, 55, 113, 115–117, 119, 156

[56] References Cited

U.S. PATENT DOCUMENTS

| | | |
|---|---|---|
| 4,839,807 | 6/1989 | Doi et al. . |
| 4,847,604 | 7/1989 | Doyle . |
| 4,851,984 | 7/1989 | Doi et al. . |
| 4,907,156 | 3/1990 | Doi et al. . |
| 4,945,476 | 7/1990 | Bodick et al. . |
| 5,072,384 | 12/1991 | Doi et al. . |
| 5,270,695 | 12/1993 | Chapman et al. . |
| 5,289,374 | 2/1994 | Doi et al. . |
| 5,293,313 | 3/1994 | Cecil et al. . |
| 5,319,549 | 6/1994 | Katsuragawa et al. . |
| 5,343,390 | 8/1994 | Doi et al. . |
| 5,359,513 | 10/1994 | Kano et al. . |
| 5,463,548 | 10/1995 | Asada et al. . |
| 5,644,649 | 7/1997 | Schoeters et al. . |
| 5,748,173 | 5/1998 | Gur . |

OTHER PUBLICATIONS

Maryellen L. Giger, Ph.D., et al, An 'Intelligent' Workstation for Computer–aided Diagnosis[1], Radiographics, vol. 13, No. 3, May 1993, pp. 647–656.

*Primary Examiner*—Scott M. Getzow
*Assistant Examiner*—Shawna J. Shaw
*Attorney, Agent, or Firm*—Oblon, Spivak, McClelland, Maier & Neustadt, P.C.

[57] ABSTRACT

A method and system for displaying medical images and computer output from various CAD schemes on the images. Images are loaded into the display system and displayed in a main viewing area. The system can display various CAD schemes, such as the automated detection of lung nodules, interstitial infiltrates, and heart size, in the case of a chest image, on the image. The method and system also display interval change (temporal subtraction) between images. Individual abnormality from CAD schemes can be viewed by clicking buttons with minified (postage stamp size) images with CAD annotation rendered into them. The images and results are then shown on a high-speed monitor. Interval change between the current and a previous image can also be chosen by clicking buttons containing minified images. Interval change between any other pair of images for a patient can be selected by choosing from minified subtraction images presented in a two-dimensional array format. A previewer next to the array permits rapid inspection of subtraction images before a subtraction set is chosen for detailed study.

54 Claims, 14 Drawing Sheets

METHOD AND SYSTEM FOR DISPLAYING MEDICAL IMAGES

The present invention was made in part with U.S. Government support under NCI, NIH and DHHS grants/contracts USPHS CA62625, CA64370, CA60187 and HL52567; and U.S. Army and DOD grant/contracts MRD DAMD 17-93-J-3021 and 71-96-1-6228. The U.S. Government has certain rights in the invention.

BACKGROUND OF THE INVENTION

1. Field of the Invention

The present invention relates to a method and system for displaying medical images and, more particularly, to a method and system for displaying medical images with computer-aided diagnosis results.

2. Discussion of the Background

In order to improve the diagnostic accuracy and consistency of radiologists' image interpretations, computer-aided diagnostic (CAD) schemes have been developed for automated detection of lesions and characterization of normal and abnormal patterns. Computer output is used as a second opinion prior to the final decisions of radiologists. CAD schemes include the automated detection of lung nodules, interstitial infiltrates, heart size, pneumothoraces and interval changes in chest radiographs; detection of masses and clustered microcalcifications in mammograms; analysis of stenotic lesions in angiograms, and analysis of risk of fracture and osteoporosis in bone radiographs.

Typically, a radiologist looks at an entire image. Often this image contains superimposed CAD results usually taking the form of some type of marker, such as an arrow, circle, triangle or square. In the case where a patient has multiple diagnosis results, the image can become obscured and difficult to read. There is a need to display images in a format where the CAD results can be viewed without interfering with the radiologist reading the image. Also, the multiple images corresponding to the CAD results are automatically sequentially displayed by the system.

Some patients have many images taken over time. Another need for radiologists is to display information so that the change in a patient's condition can be determined, i.e., the difference between two images is displayed.

SUMMARY OF THE INVENTION

An object of the present invention is to provide a novel method and system for displaying medical images.

Another object of the present invention is to display simultaneously multiple images of a subject that are simple to read and manipulate.

A further object of the present invention is to display a number of original and subtraction images simultaneously.

These and other objects of the invention are achieved by a method and system that displays an image along with corresponding ones of the same image with computer-aided diagnostic (CAD) information added. The display of the image is normally of a larger size to allow a radiologist to easily read the image while the corresponding ones of the images with the CAD information are displayed in a smaller size. The smaller images allow the radiologist to view all of the information available for the image at one time. The radiologist can select any of the corresponding smaller images to be viewed in the larger size.

The method and system can also display subtraction images. The system generates (or retrieves) subtraction images and creates corresponding smaller images displayed along with the larger image. The subtraction images allow the radiologist to rapidly view the change in condition of a patient. The subtraction images as well as the images corresponding to the CAD results can be displayed at the same time with the larger image.

In more detail, the method and system according to the invention can display computer outputs from various CAD schemes in images using a CRT monitor or an equivalent high speed, high resolution image display device, in a main viewing area. Individual abnormality detected by computer as well as the overall results with minified (postage stamp size) images are displayed on the monitor in a second viewing area. The minified images are presented as function buttons. Selecting the buttons places the image corresponding with the button in larger size in the main viewing area. Comparison of a current image with previous images together with CAD results and subtraction images are displayed in an array format.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
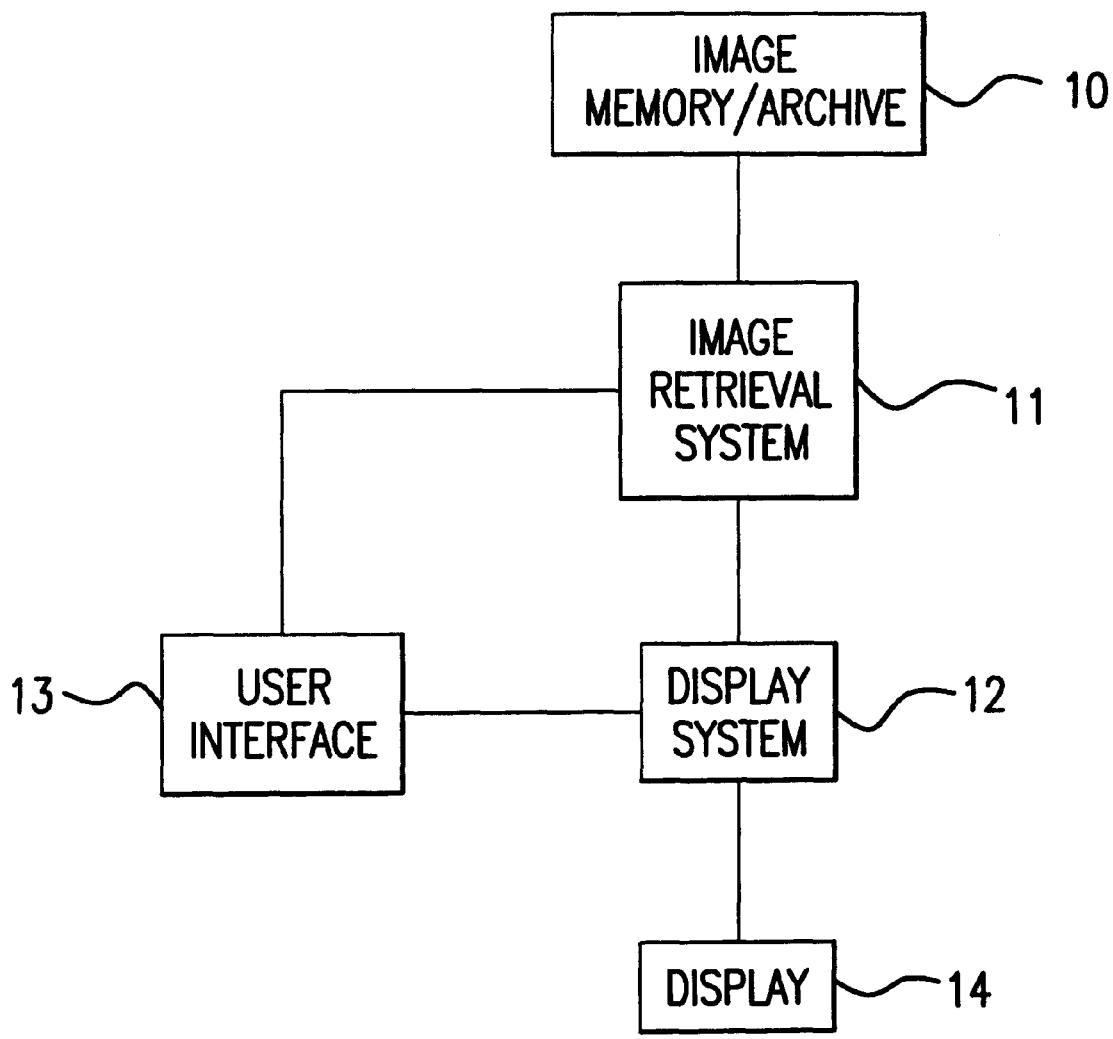
FIG. 1 is a diagram of the system according to the invention.

Referring now to the drawings, in particular FIG. 1, the preferred embodiment of the invention will be described.

FIG. 1 shows a diagram of the system according to the invention. Medical images are stored in an image memory/archive 10. The memory/archive can be an electronic, magnetic or optical storage device, or a combination of the three. For example, recently taken images could be stored in RAM or on magnetic disk while older images could be stored on optical disks arranged in a multi-disk file system.

Computer-aided diagnosis (CAD) is often performed on the images for automated detection of lesions and characterization of normal and abnormal patterns. Computer output is used as a second opinion prior to the final decisions of radiologists. CAD schemes can include the automated detection of lung nodules, interstitial infiltrates, heart size, pneumothoraces and interval changes in chest radiographs; detection of masses and clustered microcalcifications in mammograms; analysis of stenotic lesions in angiograms, and analysis of risk of fracture and osteoporosis in bone radiographs. The results of the CAD are stored with the image in the memory/archive 10 and are retrieved along with the images.

The images are retrieved using image retrieval system 11. The images can be retrieved on the basis of information added to the image such as patient name or identification, modality used to create the image, etc. The user enters this information from the user interface 13. Interface 13 can be a keyboard and pointing device, for example.

With the information received from interface 13, retrieval system 11 retrieves images from memory/archive 10 and transfers them to display system 12. Display system 12 transfers the retrieved images 12 to display 14. Display 14 is preferably a video display terminal or other high-speed, high-resolution display device. User interface 13 also provides for the entry commands, data, etc. to display system 12 to control the display of the image on display 14.

The retrieval and display systems 11 and 12 may be separate, as shown in FIG. 1, or may be a single unit. For example, a network server/computer could be programmed to perform all of the functions required of systems 11 and 12 while the user interfaces with the network server/computer via a terminal, workstation or personal computer. Also, the network server/computer can perform the functions of the retrieval system only while the display system functions are carried out by a programmed workstation or personal computer. The configuration used and division of the required functions can be adapted to the particular needs of the overall system.

Figure 2:
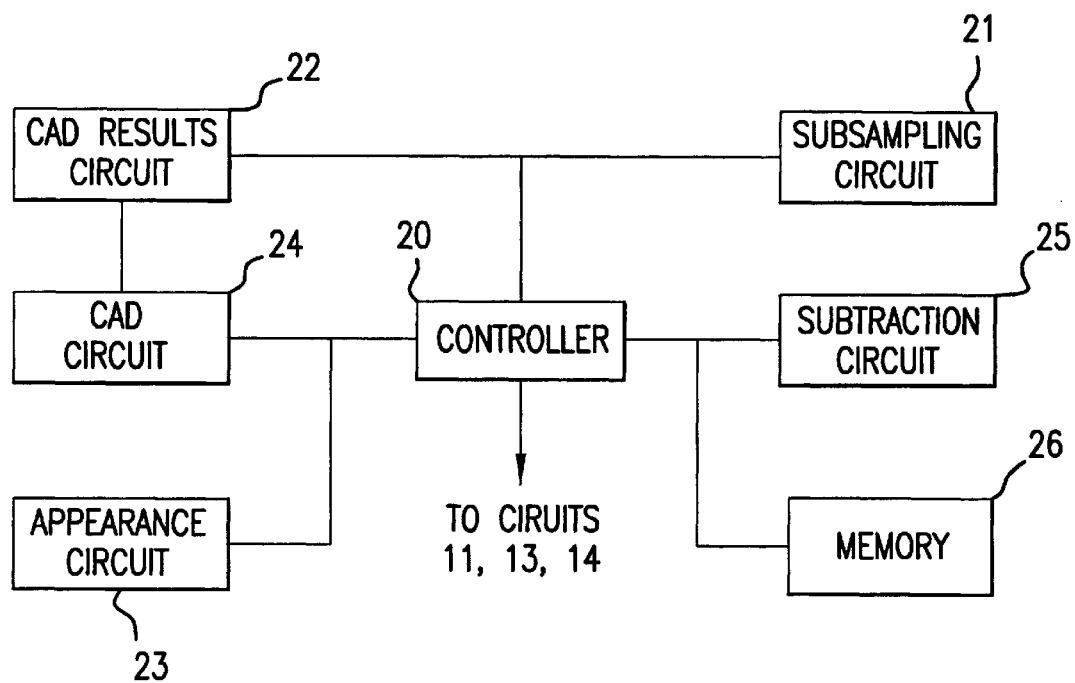
FIG. 2 is a diagram of the display system according to the invention.

A more detailed view of the display system 12 is shown in FIG. 2. System 12 has a controller 20 that controls the various circuits and the input of the images, CAD information and instructions from system 11 and interface 13 and output of the images and CAD information to display 14. System 12 has a subsampling circuit 21 to subsample patient images to produce minified versions, of the images, for example, 77 by 104 or 75 by 84 pixels. Also included in system 12 is a CAD results circuit 22 that allows CAD results (lung nodule, interstitial infiltrate or heart size, for example) to be added to the images, and an image appearance circuit 23 that allows the user to adjust parameters such as brightness and contrast of the images, magnify part of the image (zoom).

In the event that the CAD results have not been determined, the user can instruct CAD circuit 24 to perform any of the CAD functions and superimpose the results on the images.

System 12 can include a temporal subtraction circuit 25 that performs subtraction between images of a patient taken at different times. The temporal subtraction images illustrate the difference in the condition of a patient over time. A memory 26 stores images loaded into system 12, images generated by system 12 (such as the temporal subtraction images) and other information (such as CAD results).

The operation of the display and retrieval systems 11 and 12 will be described in more detail below. The following describes one manner of operating of the system using chest radiographs as the patient images to illustrate the invention. The invention is not limited to this single embodiment but is applicable to different types of images, CAD results, image manipulation, etc. The display of other images, such as mammograms or vascular images is possible with the system and method according to the invention. Further, the display system 12 of FIGS. 1 and 2 can be implemented in hardware or in software.

Figure 16:
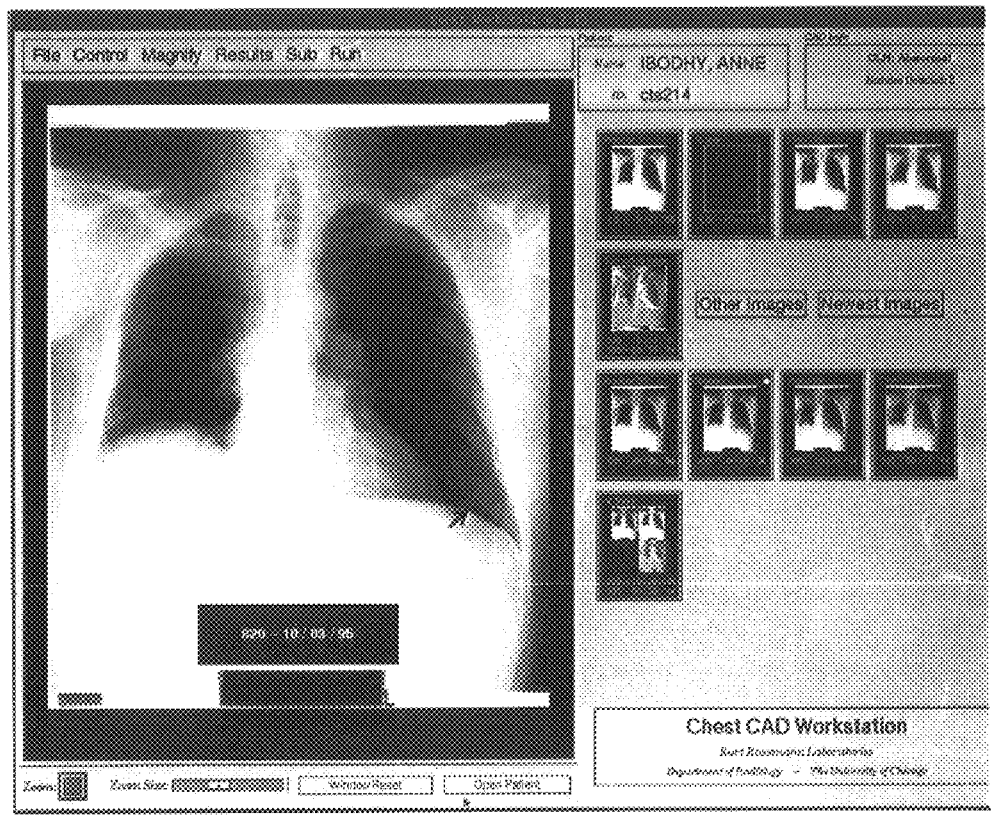
FIGS. 16–20 are illustrations of screens produced by the system according to the invention.

Illustration of actual images being viewed using the system according to the invention are shown in FIGS. 16–20. FIG. 16 shows a chest radiograph displayed in main image viewing area 31. Apparent from FIGS. 16–20, in the embodiment there are various pull-down menus (not shown) and buttons available.

First, with reference to FIG. 3, the selection of the patient and images of the patient will be discussed. To choose a patient for viewing, the user can select Open Patient in the bottom control area 36, or Patient in the File menu on the menu bar. A patient is then chosen from a list appearing in an Open Patient window. All images in the memory/archive 10 for a patient are loaded into the display system 12, including original images (those which are actually from patient exposures), along with available CAD result information stored with the images. Subtraction images, including those generated by the temporal subtraction circuit (or CAD program) 25, are also loaded. The patient's name and identification (ID) information, also retrieved from memory/archive 10 along with the images, are shown in the patient information area 33.

The images appear in greyscale, with the original image values mapped to display intensity. The user can modify the contrast and brightness, collectively called windowing, using appearance circuit (or program) 23.

Figure 19:
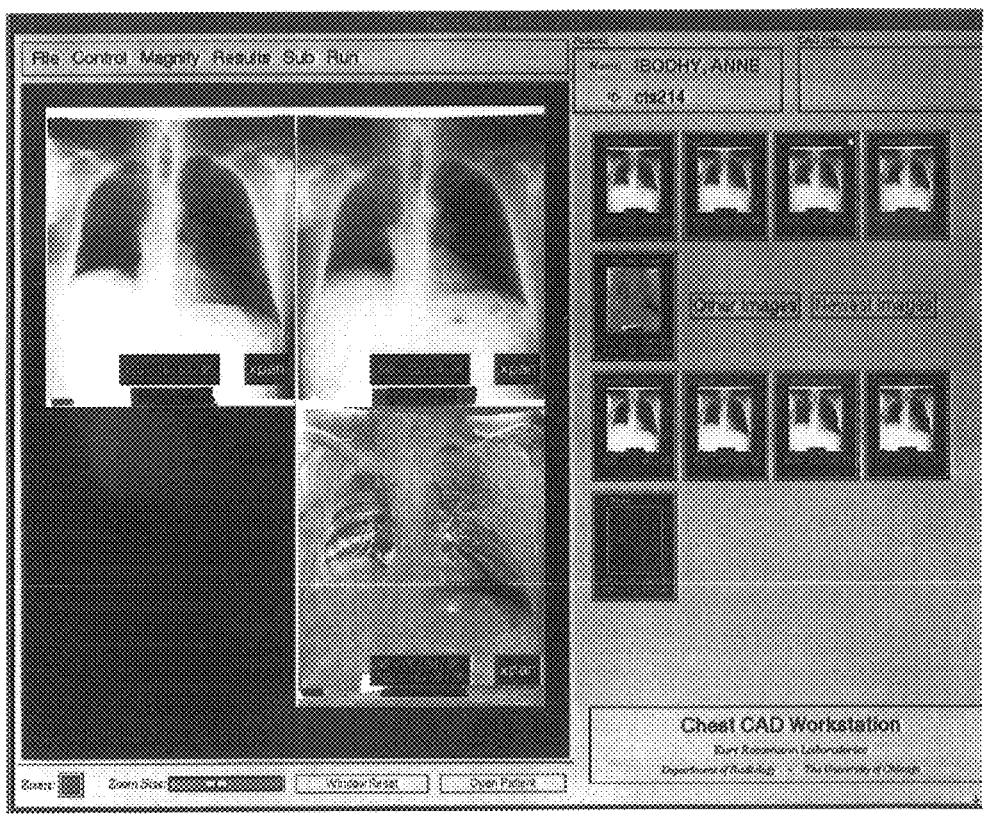

If one or more subtractions exist (or are generated) between the patient's newest original image in the system ("current") and an older image ("previous"), the subtraction set involving the most recent previous original image is automatically chosen for study. The three images in the set (previous, current, and subtraction) are shown simultaneously in area 31 in the in the "All Three" configuration (FIG. 19). Area 32 shows buttons corresponding to the subtraction configuration, enabling the user to display any of the images in the study, along with CAD results for the current and previous images.

If no subtractions exist between the current image and a previous image, the current image is shown alone in the main viewing area 31. Area 32 then shows buttons corresponding to the single image configuration (described below).

If a subtraction set is being studied, the CAD/Image Selection Area 32 allows the user to choose the newer original image or older original image, along with nodule, interstitial infiltrate, and heart size CAD. The subtraction image can be chosen to be displayed alone, or the entire subtraction set (newer, older, and subtraction images) can be chosen for display. If a single image is being studied, the user can, for example, display the image without any CAD annotation, or with one or more of nodule, interstitial infiltrate, or heart size annotations.

If CAD is selected for an image (from Menu Bar 35 or CAD/Image Selection Area 32), markers are shown over the image (FIG. 17), and text corresponding to CAD output is shown in the CAD Information Area 32. The CAD/Image Selection Area 32 contains combinations of images and annotations that the user can view. Annotations are CAD results for a single image. For a chest radiograph these can include nodule detection, interstitial infiltrate detection, and heart size detection CAD schemes. As shown in FIG. 16, 3 CAD results for the images Previous 1 and Previous 2 are displayed. Temporal subtraction is not displayed with these images but separately.

The buttons in area 32 contain miniature versions of the actual image(s), obtained from the subsampling circuit 21, and CAD annotations that would be shown in the main image viewing area 31 if the image(s) were selected.

The CAD output for the image currently being shown in the main image viewing area 31 can also be chosen from Menu bar 35, if desired. Additionally, the subtraction and the entire subtraction set being studied can also be selected for display through options in the Menu bar 35.

If Other Images is selected, the Other Images/Subtraction Selection Screen (FIG. 13) appears, showing all combinations of images and subtractions available for this patient. The user can select one of the images which returns the system to area 31 and the selected image is displayed.

To select the patient's newest image for study, the user can press the Newest Images button. The main screen appears just as it would if the patient was just loaded. Hence, if there is a subtraction set available between the current image and one of the previous images, the newest set is chosen for study; otherwise, the current image alone is chosen for study.

Now, the features of the invention will be described in more detail. The main screen 30, shown in FIG. 3, is where the user can perform an in-depth study of a subtraction set or a single image for a patient. FIG. 3 shows the main screen generated on display 14 by the display system 12. Using this screen and the interface 13, the user can enter commands or information to control the systems 11 and 12 and is where the user typically performs the majority of his/her work with the system. There are seven components that are associated with main screen 30: main image viewing area 31, CAD/Image selection area 32, patient information area 33, CAD information area 34, menu bar 35 and bottom control area 36. Not shown in FIG. 3 is the patient selection window which overlays main screen 30 when selected. It is noted that in FIGS. 16–20 a fictitious name, Anne Ibodhy, is used.

Figure 3:
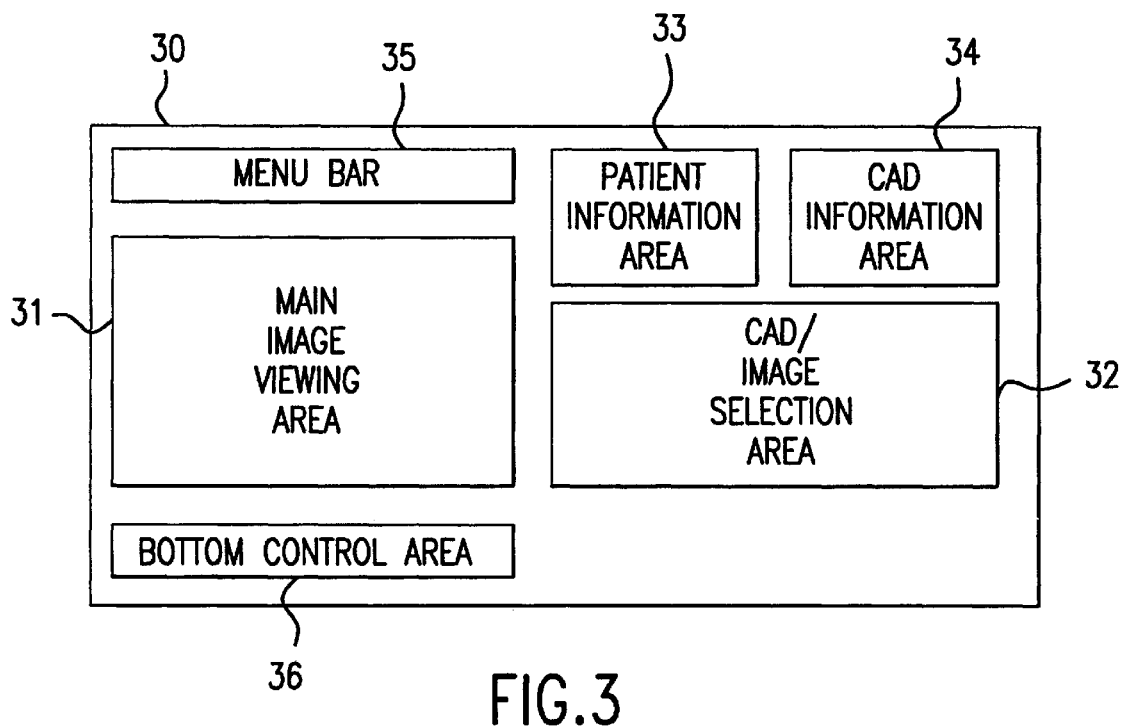
FIG. 3 is a diagram of the main screen produced by the display system according to the invention.

In FIG. 3 there are two primary display areas, the main image viewing area 31 and the CAD/Image selection area 32. In area 31 the image or images being displayed are shown while area 32 allows one to select and manipulate the image or images displayed in area 31. The patient information area 33 displays information about the patient whose image or images are being displayed. The CAD information area 34 indicates computer-aided diagnosis information, such as whether the image is abnormal and contains an area suspected of being cancerous. The menu bar 35 provides tools to manipulate the images as well as information displayed in the other areas, while control area 36 allows the user to modify the image viewing characteristics as well as other tasks such as selecting a new patient.

The main image viewing area 31 is where the user can inspect a patient's original image or a subtraction set in detail. Images are presented on the system with original image density mapped to screen brightness. The way the system does this is dependent upon the current windowing values (selected by the user via appearance circuit 23) which are brightness and contrast settings. The user can adjust the brightness and contrast. As an example, this can be performed by either moving a mouse over the image(s) with a mouse button pressed down, or by selecting Windowing from the Control menu in the menu bar (not shown). In this embodiment, the contrast and brightness affect every image on the screen, including the miniature versions in the buttons.

Each image in the system has identification information. In this embodiment a day number is assigned to every original image. This is a unique number given to an examination, and is closely related to the date. To aid the user, the day number is shown near the bottom of all displayed images in main area 31 (FIG. 16).

The system allows the user to magnify part of the displayed image(s) and annotation using a semi-continuous zoom feature. It is selected from control area 36 as a Zoom button or as the Zoom option in the Magnify menu (not shown). The zoom feature is disabled either by pressing the Zoom button again or choosing the None option in the Magnify menu.

Figure 4:
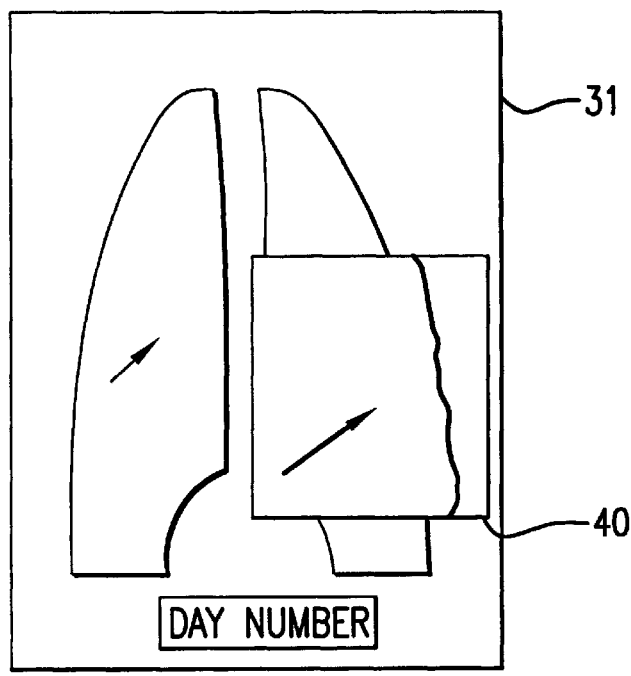
FIG. 4 is a diagram illustrating a magnification operation according to the invention.

When zoom is enabled, the appearance circuit 23 generates a magnify area 40 inside the image displayed in area 31, showing the image and annotation at larger size, as shown in FIG. 4. The magnify area is generated using subsampling or pixel replicating as necessary. The user can move the magnify square, for example, with the left mouse button. The zoom factor can be increased or decreased, for example, by pressing the right mouse button and moving the mouse. The feedback to the user is almost immediate.

The proportion of zoom square size in relation to the image size can also be adjusted. In the system this is accomplished by moving the Zoom Size slider (FIG. 16) in the control area 36. As the user moves the slider to the left, the zoom square gets smaller; as the slider is moved to the right, the zoom square grows. When the slider is moved all the way to the right, the entire image display area effectively becomes a large zoom square.

In area 32 the system creates buttons having miniature images. An image and the associated CAD results are displayed. In the embodiment these are displayed in left-to-right fashion but other arrangements are possible. To view the CAD results for an image, for example, lung nodule detection, the user either presses the Nodule button next to the image of interest in CAD/Image selection area 32 or chooses the Nodule option in the Results menu (not shown).

Figure 5:
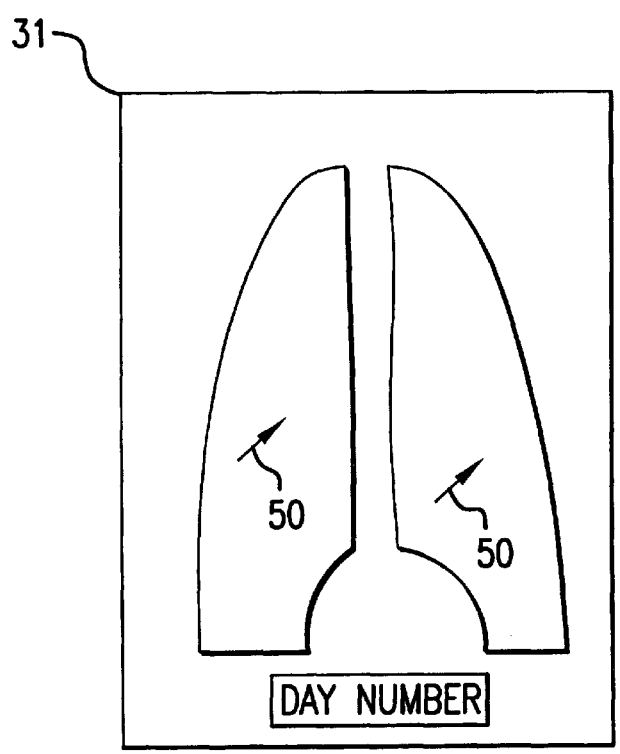
FIG. 5 is a diagram of a image having superimposed computer-aided diagnostic information indicating nodules.

An example of the resulting main image viewing area 31 is shown in FIG. 5. The image is displayed with arrows 50 indicating suspicious areas. As shown in FIG. 16, the CAD information area 34 indicates whether the results are normal (no nodules present) or abnormal (one or more nodules present). The number of nodules detected is also displayed.

Figure 6:
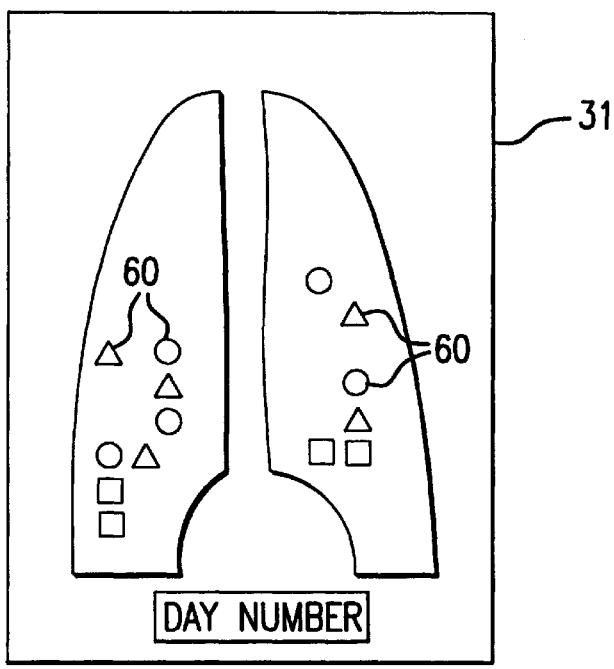
FIG. 6 is a diagram of a image having superimposed computer-aided diagnostic information indicating interstitial infiltrates.
Figure 17:
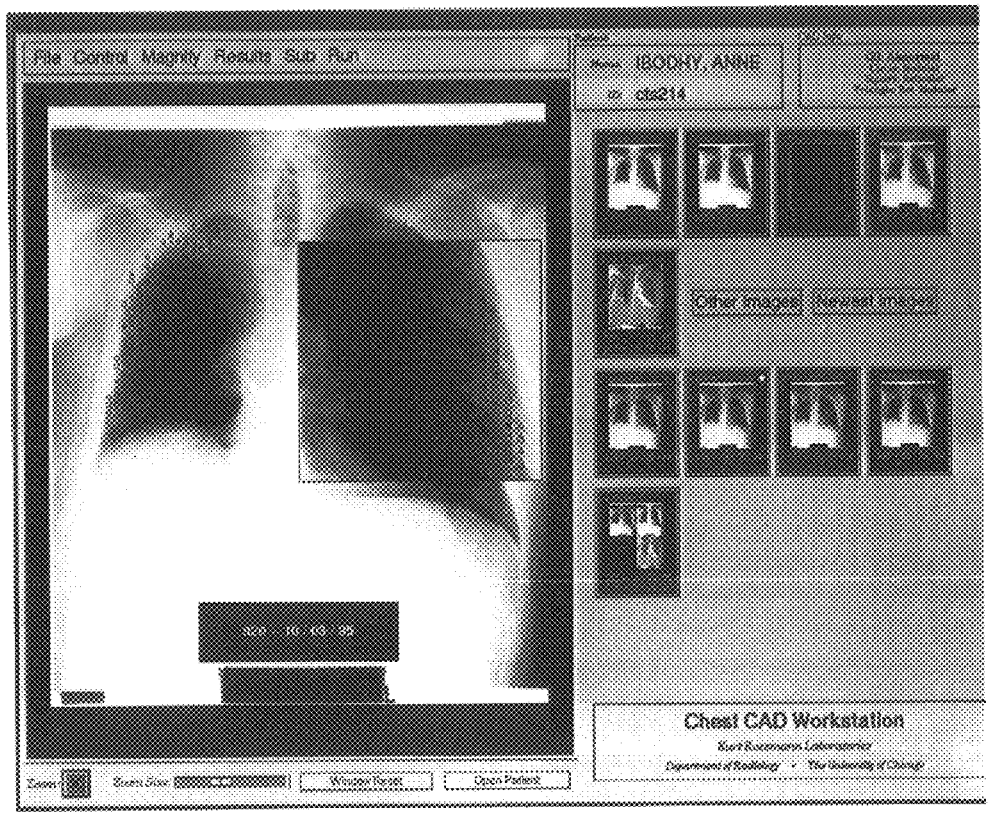
Figure 18:
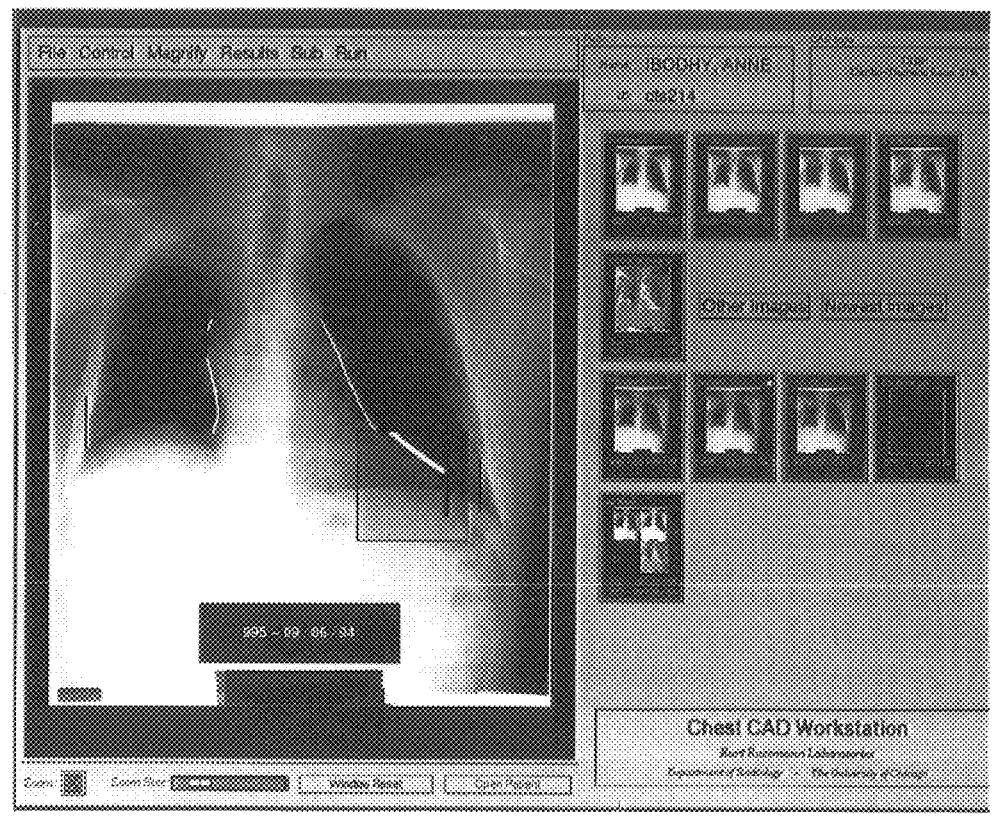

To view the results of interstitial infiltrate detection for a patient's image, the user either presses the interstitial button next to the image of interest in the CAD/Image selection area 32 or chooses the Interstitial option in the Results menu (not shown). An example of interstitial infiltrate CAD display is shown in FIG. 6. Markers 60 are placed over suspicious regions of interest in the image. Circles indicate nodular infiltrate regions, squares indicate reticular infiltrate regions, and triangles indicate reticulonodular infiltrate regions. A legend defining the shapes appears in the CAD information area 34 (FIG. 17).

A message is placed in the CAD Information area 34 based upon predetermined criteria. For example, if more than onequarter of the regions of interest are abnormal, the results for the image are considered abnormal; otherwise, the results are considered normal.

Figure 7:
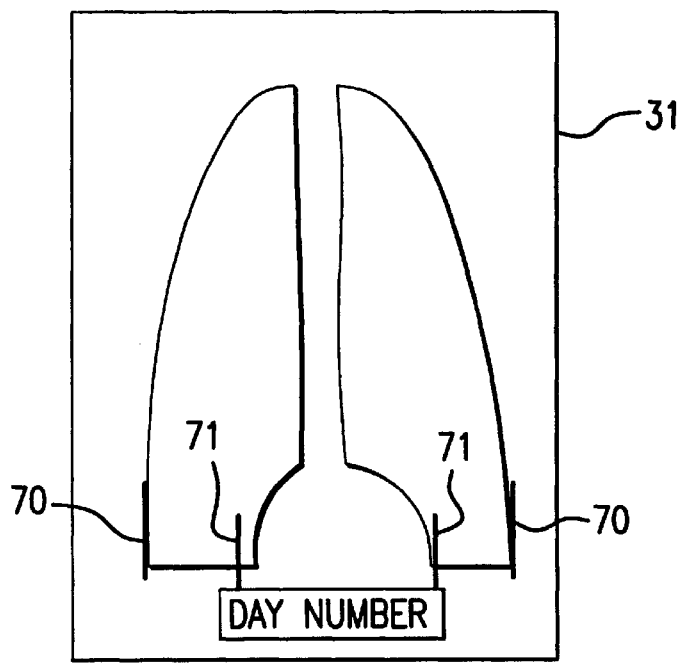
FIG. 7 is a diagram of a image having superimposed computer-aided diagnostic information indicating heart size.

To view the results of heart size detection for an image, the user either presses the Heart Size button next to the image of interest in the CAD/Image selection area 32 or chooses the Heart Size option in the Results menu (not shown). An example of heart size display is shown in FIG. 7. The image can be marked in different ways. For example, the detected heart outline can be shown on the image. Two vertical bars 70 can indicate the edges of the thorax. Two additional vertical bars 71 can indicate the positions at the extreme edges of the heart where the heart size detection routine measured the cardiothoracic ratio. The measured cardiothoracic ratio is placed in the CAD information area 34.

When a subtraction set is being studied, the user can choose the subtraction image for viewing either by pressing the Subtraction button in the CAD/Image selection area 32 or by choosing the Sub option in the Sub menu (not shown). The day number displayed at the bottom of the subtraction image is actually a combination of two day numbers: the newer day number, then a minus sign, then the older day number.

Figure 8:
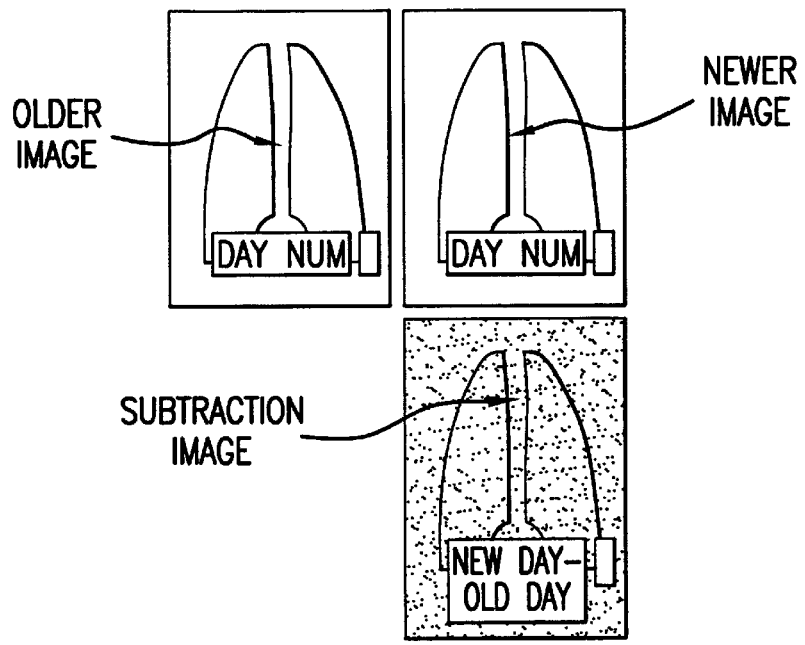
FIG. 8 is a diagram illustrating subtraction images according to the invention.

The system is also capable of showing the newer, older, and subtracted images all at the same time, the "subtraction set combination". The resulting configuration of images is shown in FIG. 8. To cause the subtraction set combination of images to appear in the main image viewing area 31, the user can either choose the All Three button (having the subtraction set combination in miniature) in the CAD/Image selection area 32 or select the All button in the Sub menu (not shown).

Figure 9:
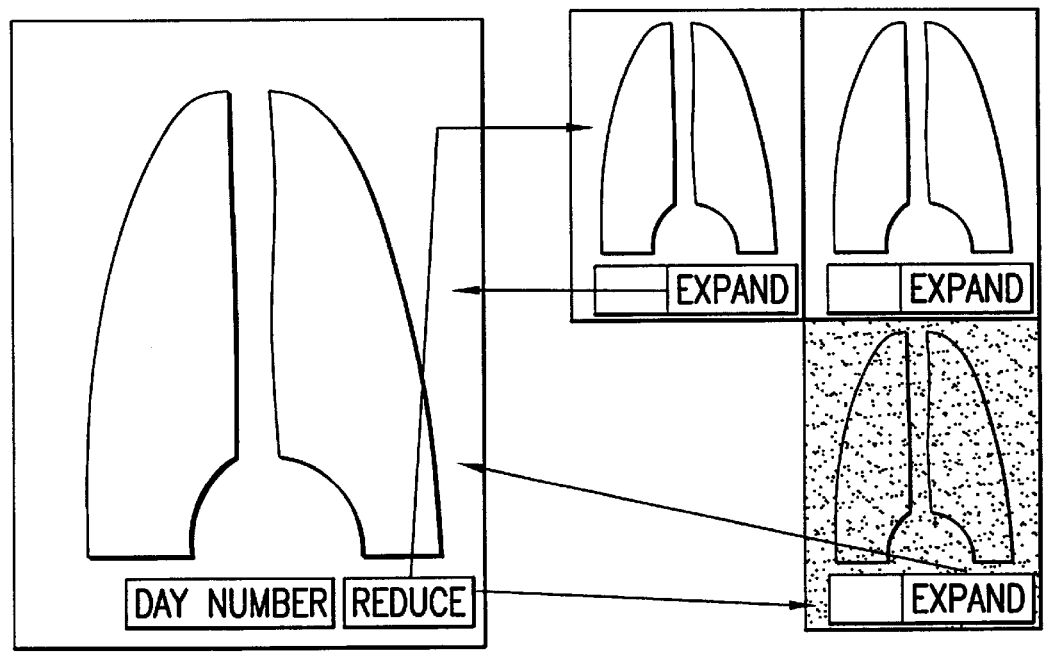
FIG. 9 is a diagram illustrating the manipulation of subtraction images.

When the user is performing a study on a subtraction set, the CAD/Image selection area 32 will present the subtraction configuration, which is one way for the user to choose whether the newer image, older image, subtraction image, or all three images at once will be viewed. However, there is also another mechanism available. If the user is viewing the newer, older, or subtraction image without annotation, there is a button near the bottom right of the image labeled "Reduce" (FIG. 9). Selecting this button causes all three images to be shown simultaneously, as described in the previous subsection. When all three images are displayed simultaneously, there are small buttons in the lower right corners of the three images labeled "Expand", which will cause the newer, older, or subtraction image to be shown individually (FIG. 19).

The CAD/Image selection area 32 contains many buttons with images and text on them. Two buttons are without images, the Other Images and Newest Images buttons. The buttons with the images on them represent combinations of images and annotations (CAD results) that convey information to the user in the main viewing area. There are two configurations of buttons used in the area 32, depending upon whether a subtraction set or a single original image is being studied.

Figure 10:
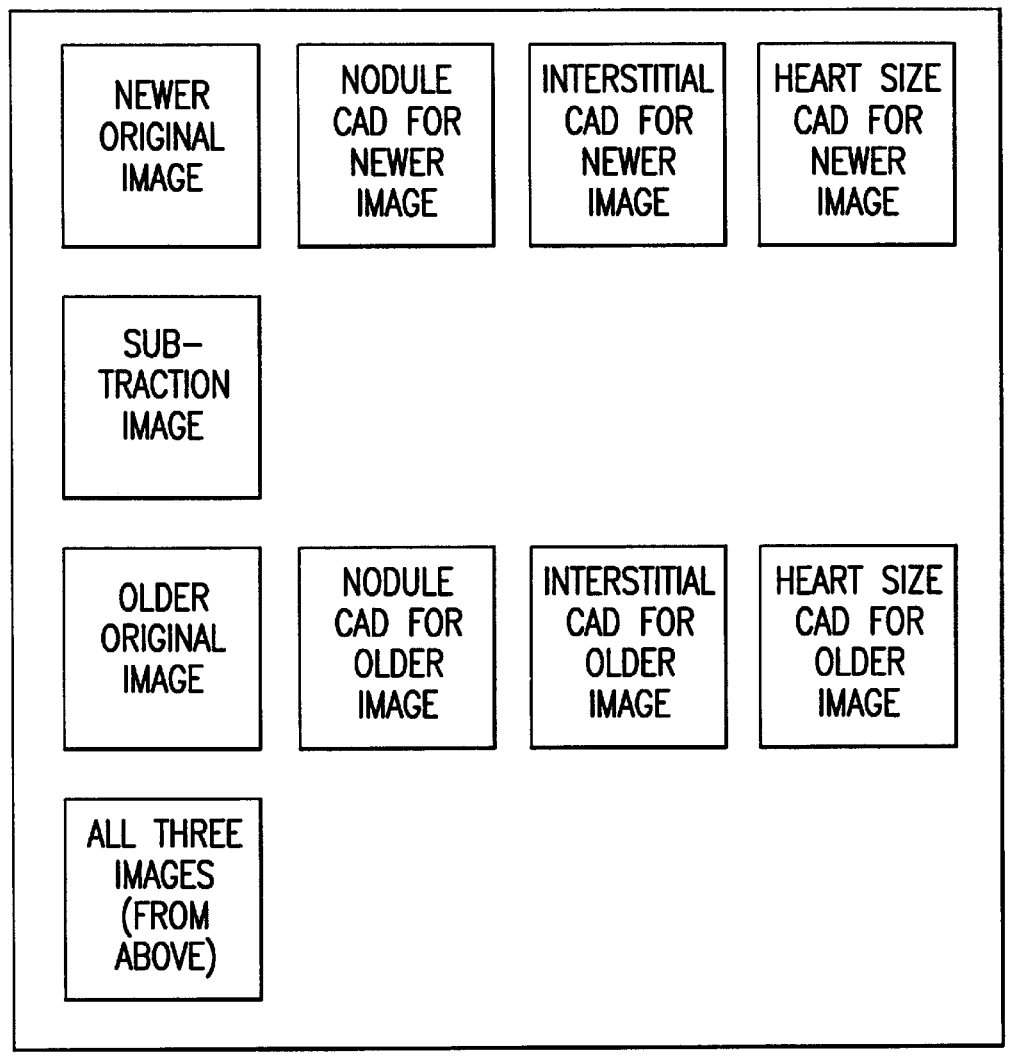
FIG. 10 is a diagram illustrating the subtraction configuration.
Figure 11:
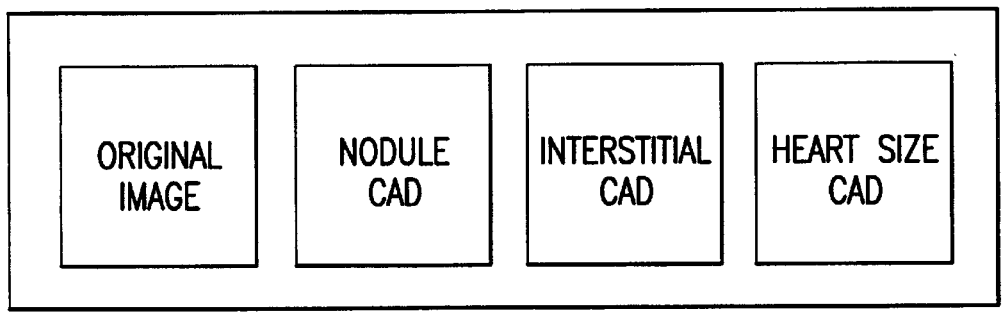
FIG. 11 is a diagram illustrating the single image configuration.

If a subtraction set is being studied, the buttons appear in the "Subtraction Configuration", shown in FIG. 10. Otherwise, the buttons appear in the "Single Image Configuration", shown in FIG. 11. In either configuration, buttons corresponding to original patient images are on the left ends of the rows with multiple images. Pressing one of these buttons will display the image in the main viewing area with no results superimposed on the image.

The buttons corresponding to the Nodule, Interstitial Infiltrate, and Heart Size CAD results are located to the right of the original patient image buttons. Pressing one of these will cause the image with the appropriate results superimposed to appear in the main viewing area 31.

Pressing the Subtraction button will put the subtraction image (representing the subtraction of newer minus older image) in the main viewing area. Pressing the All Three button will cause all three images in the subtraction set to be displayed in the main viewing area.

The buttons contain a minified image representation of what will be shown in the main viewing area if the button is pressed. When one of the buttons is pressed, the minified image is removed from the button, and is replaced by a gray frame (FIG. 19). This gives feedback to the user as to which image(s) and CAD results are being viewed. Pressing the same button a second time causes the system to toggle between the display mode indicated on the button and the former display mode.

Figure 12:
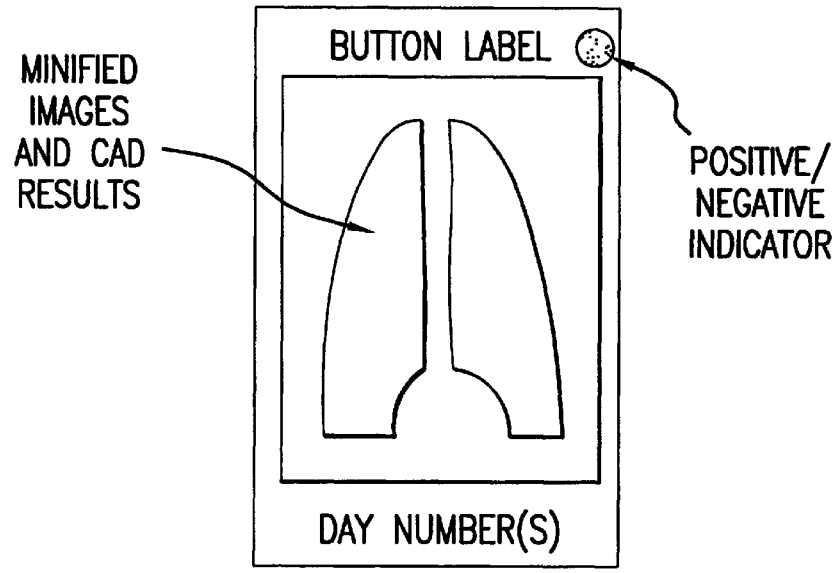
FIG. 12 is a diagram of a button in the CAD/Images Selection area.

The anatomy of a button in the CAD/Image Selection Area is shown in FIG. 12. There are several areas of note: the label, the minified image, the day number(s), and the positive/negative indicator. Original Image buttons have labels such as Current (the newest image for this patient in the system), Previous 1 (the second-newest image), Previous 2, and so forth. Nodule CAD buttons have the label Nodule, Interstitial Infiltrate CAD buttons have the label Interstitial, and Heart Size CAD buttons have the label Cardiomegaly. The Subtraction button has the label Subtraction, and the button which shows all the images in a subtraction set is labeled All Three. Other suitable labels may be used.

The buttons have a minified image, small versions of what would be shown in the main viewing area if the button were pressed, produced by subsampling circuit 21. Hence, the actual images and annotations are rendered into the button, being subsampled to fit in the button size, for example, approximately 70×85 pixels. This permits the user to obtain a rough view of the heart outline, for example, by simply inspecting the Heart Size button. For the All Three button, all three subtraction set images are rendered into the button (FIG. 16).

The buttons corresponding to the original images and the single-image CAD results show the day number of the image at the bottom of the button. The Subtraction and All Three buttons show the day numbers of both original images in the subtraction set at the bottom.

The nodule and interstitial infiltrate detection CAD programs produce results that can be directly inferred as "positive" or "negative." As an additional cue to the user, the system places a dot in the upper-right portion of the buttons corresponding to the nodule and interstitial infiltrate CAD schemes. The color of the dot can be used to differentiate between the two. For example, if the dot is red, the corresponding CAD scheme indicated a positive result. A green dot shows that the test indicated a negative result. These indicators allow the user to infer the results of the detection without actually viewing the associated images/annotations in the main viewing area.

The Control Area 36 is located beneath the main image viewing area 31 and contains frequently-used tools. The first tool instructs the system to specify whether the zoom window should be active. The second tool is a slider bar that controls the size of the zoom window relative to the size of the image(s), as discussed above. The third tool instructs the system to reset the windowing (contrast and brightness) to default levels. The fourth tool activates the Patient Selection Window so that the user can open another patient.

Menu bar 35 is a largely standard X-Windows type menu bar. Most of the options in the menus duplicate the functionality of other parts of the interface. They are provided to give the system flexibility. In the embodiment six menus are available: File, Control, Magnify, Results, Sub, and Run. The menus and their contents will be briefly discussed in turn.

The File Menu, contains four system commands: Patient, Print Buffer, Analysis, and Quit. The Patient option brings up the Patient Selection Window, duplicating the Open Patient button in the Control area 36. The Print Buffer option allows the user to print an image or multiple images. The Analysis submenu gives the user tools to investigate the grey levels in an image, such as histogram analysis or gray-level profiling in a region-of-interest. The Quit button exits the system.

The Control Menu contains five system commands: Windowing, Other Images, Newest Images, Hide Buttons, and Hide Dates. Choosing the Windowing option will pop up a windowing widget. The Other Images and New Images options duplicate the functionality of the buttons with the same name in the CAD/Image Selection area 32. The Hide Buttons option will hide buttons which appear over the images in the main image viewing area 31. The Hide Dates option will get rid of the day number labels which appear on the images in the main image viewing area, allowing the user to see detail underneath. Choosing each of these last two options again will make the buttons/dates reappear.

The Magnify Menu contains two system commands: Normal and Zoom. These correspond to the action of the Zoom toggle button in the Control area 36.

The Results Menu contains four items: None, Nodule, Interest, and Heart Size. If an image is currently being displayed in the main image viewing area 31, these options will show it with the corresponding CAD results. These options are related to buttons in the CAD/Image Selection Area.

The Sub Menu contains four items: Newer, Sub, Older, and All. If a subtraction set is currently being studied, the Newer button shows the newer original image (without CAD results superimposed), the Older button shows the older original image (without CAD results superimposed), the Sub button shows the subtraction image, and the All button shows the subtraction set combination of images. These options correspond to buttons in the CAD/Image selection area 32.

The last menu, Run, contains the instruction for the system to run CAD for an image, using circuit 24, in the unusual case that it was not performed automatically.

By default, upon image load, the most recent subtraction set involving the first image is chosen for study. If such a subtraction set is not available, only the current (newest) original image is chosen for study. If a radiologist wanted to view another subtraction set or simply another original image for the current patient, the system provides the Other Image/Subtraction Selection Screen for this purpose. The screen is selected either by choosing the Other Images button in the CAD/Image selection area 32 on the main screen 30 or by choosing Other Images from the Control menu on the menu bar 35. Selecting Newest Images from the main screen will select the same set of images for study as would be selected if the patient was just loaded.

Figure 13:
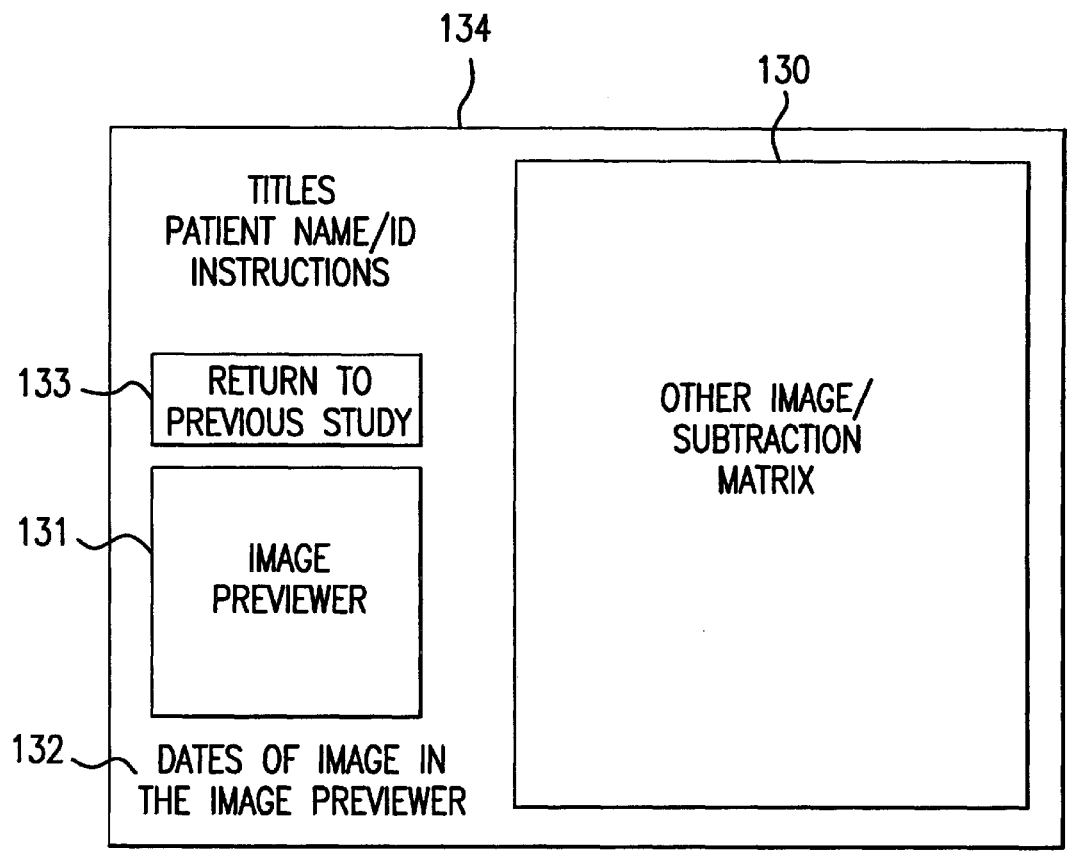
FIG. 13 is a diagram of the Other Images/Subtraction Screen.
Figure 14:
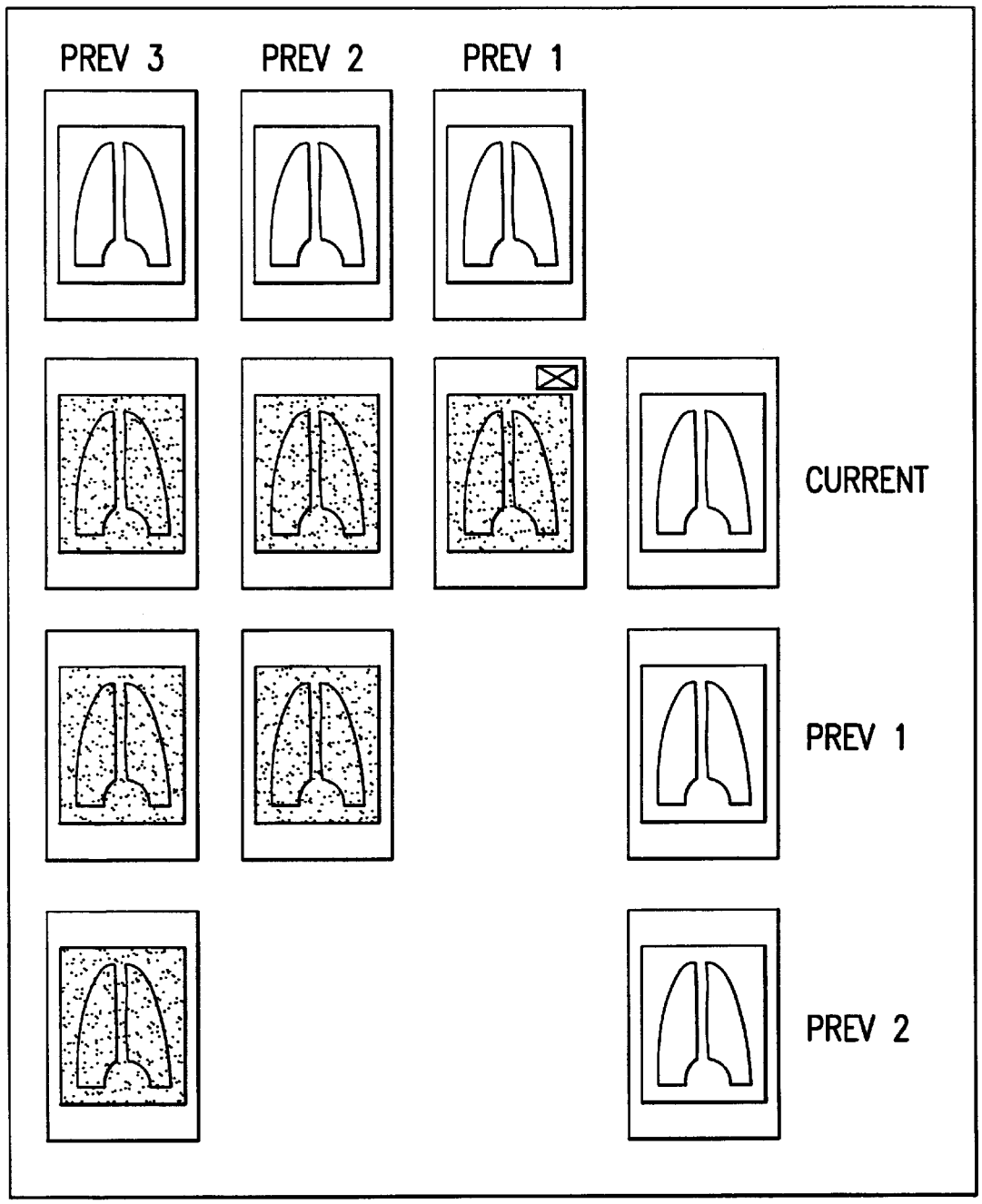
FIG. 14 is a diagram of the subtraction image matrix according to the invention.
Figure 20:
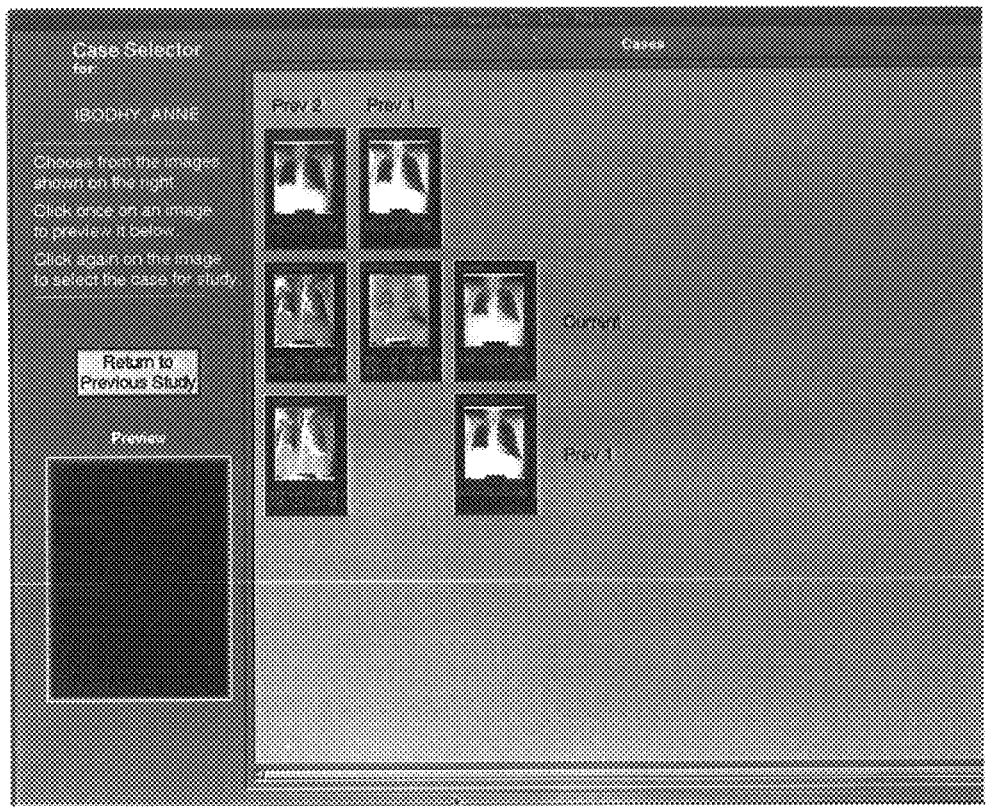

The other Image/Subtraction Selection Screen 134 produced by the system is shown in FIG. 13. The screen displays all available original images in button form and completed subtractions for the chosen patient. The images are displayed in a matrix form as shown in FIGS. 14 and 20. Selecting one of the images, by pressing a button once, causes the image corresponding to the button (either an original image or a subtraction) to be shown in the Image Previewer 131.

Image Previewer 131 is generally large enough for the user to identify the image as either the correct original image (if applicable) or as a "good" subtraction. The day numbers corresponding to the image or subtraction are shown in area 132 below the Image Previewer 131.

The original image or subtraction displayed in the Previewer 131 can be selected for study in the main screen 30. This can be done by either clicking again on the corresponding button in the Other Image/Subtraction matrix screen 130 or clicking on the Image Previewer 131. The Return to Previous Study button 133 will bring back the previous main screen 30 without altering the choice of images being studied.

A schematic for the Other Image/Subtraction Matrix is shown in FIG. 14. All of the patient's original images (CURRENT, PREV 1, and PREV 2), except the oldest, appear along the right side of the matrix. All of the original images, except the newest (CURRENT), are displayed along the top. These row and column headers are labeled with sequential image numbers. The newest image is labeled "CURRENT", the second newest image is labeled "PREV 1", the third newest image is labeled "PREV 2", and so forth. Subtractions created from each pair of original images are shown at the intersection of 25 the pair of images. The subtractions are prepared by circuit or are retrieved from storage.

The system also indicates the original image or subtraction set most recently studied by the user in the main viewing area 31. This can be done, for example, with small red box with an X through it placed in the upper-right corner of the buttons (FIG. 14). For instance, if the user was studying the subtraction set PREV 1–PREV 2 in the main viewing area 31, the subtraction at the intersection of these two rows would have a marker on it.

Figure 15A:
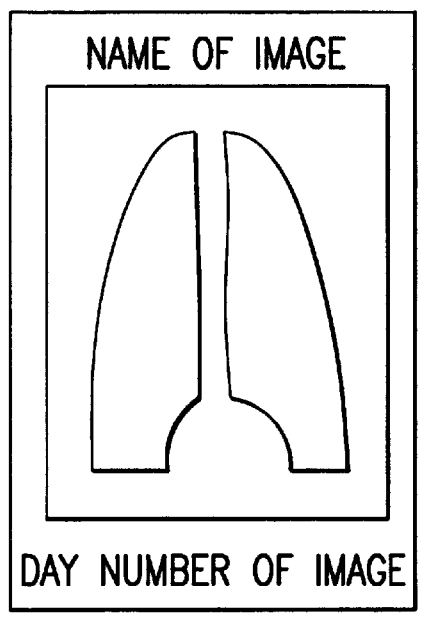
FIGS. 15A and 15B are diagrams of original image and subtraction image buttons, respectively.

For the buttons which correspond to original images, the image name (CURRENT, PREV 1, etc.) The image name appears at the top. The center of the button contains a minified version of the original image to which the button corresponds, and at the bottom is the day number of the image. The minified image consists of the actual image data subsampled down by circuit 21, for example, to size of approximately 77×104 pixels. An illustration of original image button layout is shown in FIG. 15A (and FIG. 20).

Figure 15B:
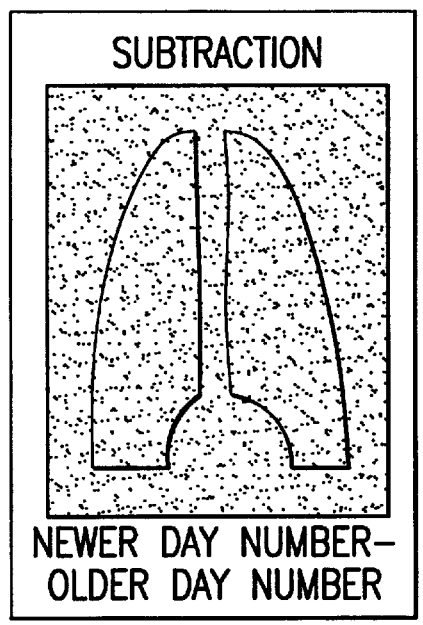

The buttons which correspond to subtractions have the word "Subtraction" at the top of the button. A minified image lies in the middle of the button, also prepared by circuit 21. Again, the minified image contains the actual subtraction image subsampled down, for example, to a size of approximately 77×104 pixels. At the bottom of the button are the day numbers of the original images that have been subtracted to create this image. An illustration of subtraction image button layout is shown in FIG. 15B.

Since there are potentially many combinations of images for a given patient, there may be potential subtractions which have not been performed yet. By default, upon digitization of a new image, three subtractions are run:

1) Current—Previous 1
2) Current—Previous 2
3) Current—Previous 3

When the Other Image/Subtraction Matrix is shown, any buttons which correspond to non-existent subtractions have an indication such as "Not Available" where the minified image would normally be. If the user presses one of these buttons, the system will prompt whether the subtraction should be performed. If the user clicks "Yes", the subtraction will be run in the background by circuit 25. If the user is still studying this patient when the subtraction is completed, it will be loaded and displayed in the matrix.

Obviously, numerous modifications and variations of the present invention are possible in light of the above technique. It is therefore to be understood that within the scope of the appended claims, the invention may be practiced otherwise than as specifically described herein. Although the present invention is described with relation to a windows approach to displaying and manipulation the images where a user selects images and commands from buttons and pull-down menus with a pointing device, the invention is not limited to this particular approach. Also, the buttons could be arranged in a different configuration and different information could be displayed. For example, the buttons contain minified images to allow the user to preview the image, in miniature form, to assist in selecting images. The particular size and shape of the button can be varied.

The invention is also described with respect to chest images and particular CAD techniques. The invention is applicable to other images and other CAD techniques.

What is claimed as new and desired to be protected by Letters Patent is:

1. A computerized method of displaying medical images, comprising:
   obtaining a first medical image representative of an anatomy as said anatomy existed at a first point in time;
   obtaining a second medical image representative of an anatomy as said anatomy existed at a second point in time temporally spaced from said first point in time;
   obtaining a temporal subtraction image in which one of said first and second medical images of said anatomy is subtracted from the other thereof, said temporal subtraction image highlighting changes occurring in said anatomy between said first and second points in time;
   obtaining at least one first diagnostic image of said first medical image, each diagnostic image including said first medical image having superimposed respective diagnostic annotations indicative of the results of computer aided diagnosis superimposed on said first medical image, said diagnostic annotations being displayed in spatial relation to respective portions of said anatomy;
   displaying one of said first medical image, said second medical image, said temporal subtraction image and said first diagnostic image in a first display area of a first display screen; and
   displaying said first medical image, said second medical image, said temporal subtraction image and said first diagnostic image including said respective diagnostic annotations in a second display area of said first display screen for visual comparison with the image displayed in said first display area.

2. A method as recited in claim 1, comprising:
   displaying said first and second medical images, said temporal subtraction image and said first diagnostic image including said respective diagnostic annotations in miniature in said second display area in comparison with a size of the image displayed in said first display area.

3. A method as recited in claim 1, comprising:
   obtaining a second medical image of said anatomy;
   obtaining a subtraction image in which one of said first and second medical images of said anatomy is subtracted from the other thereof; and
   displaying said subtraction image and said first and second medical images.

4. A method as recited in claim 3, comprising:
   displaying said temporal subtraction image grouped with said first and second medical images.

5. A method as recited in claim 3, comprising:
   displaying said first and second medical images, said temporal subtraction image and said first and second diagnostic images including said respective diagnostic annotations in miniature in said second display area in comparison with a size of the image displayed in said first display area.

6. A method as recited in claim 5, comprising:
   displaying miniature of said first and second diagnostic images in association with respective miniature of said first and second medical images in said second display area.

7. A method as recited in claim 5, comprising:
   displaying in said second display area respective display selection function buttons for each of said at least first and second medical images and said temporal subtraction image; and
   displaying in said first display area a respective one of the first and second medical images and said temporal subtraction image upon activation of the respective display selection function button.

8. A method as recited in claim 7, comprising:
   displaying said first and second medical images and said temporal subtraction image superimposed in miniature on respective of said display selection function buttons at least when the respective display selection function button is not activated.

9. A method as recited in claim 8, comprising:
   altering the display of a miniature image in a selected display selection function button displayed in said second display area upon activation of the selected display selection function button.

10. A method as recited in claim 9, comprising:
    providing in said second display area an all-three display selection function button which when activated results in display of the first and second medical images and said temporal subtraction image in said first display area; and
    displaying said first and second medical images and said temporal subtraction image in said first display area upon activation of said all-three display selection function button.

11. A method as recited in claim 9, comprising:
    indicating in at least one of said function buttons a diagnostic decision.

12. A method as recited in claim 5, comprising:
    obtaining identification information corresponding to said medical image; and
    displaying said identification information with said medical image.

13. A method as recited in claim 5 comprising:
    displaying in said first screen diagnostic result information corresponding to the displayed diagnostic image displayed in said first display area.

14. A method as recited in claim 3, comprising:
    displaying in said second display area a respective display selection function button for each diagnostic image and for said first and second medical images and for said temporal subtraction image such that upon activation of said display selection function button the respective image corresponding thereto is displayed in said first display area; and displaying the image corresponding to the activated display selection function button in said first display area upon activation of the respective display selection function button.

15. A method as recited in claim 14, comprising:

displaying in miniature superimposed on each said display selection function button respective of said diagnostic images, said first and second medical images, and said temporal subtraction image in said second display area at least when the respective display selection function button is not activated.

16. A method as recited in claim 15, comprising:

altering the display of a miniature image superimposed on a selected display selection function button upon activation of the selected display selection function button.

17. A method as recited in claim 16, comprising:

indicating in at least one of said function buttons a diagnostic decision.

18. A method as recited in claim 15, comprising:

providing in said second display area an all-three display selection function button which when activated results in display of the first and second medical images and said temporal subtraction image in said first display area; and displaying said first and second medical images and said temporal subtraction image in said first display area upon activation of said all-three display selection function button.

19. A method as recited in claim 15, comprising:

displaying in said second display area an other-images display selection function button which when activated produces a second screen in which plural images of said anatomy are arranged in a matrix, said matrix including a first row in which medical images of said anatomy obtained at different points in time are arranged, a second row including at one end of said second row a medical image laterally offset with respect to said medical images of said first row and temporal subtraction images respectively resulting when one of the medical images of the first row and the laterally offset image of said second row is subtracted from the other of the medical images of the first row and the laterally offset image of said second row, each temporal subtraction image being displayed vertically aligned in a column with the respective medical image of the first row from which the respective subtraction image was derived; and displaying said second screen upon activation of said other-images display selection function button.

20. A method as recited in claim 19, comprising:

said second screen having first and second display areas;

displaying display selection function buttons in said second display area of said second screen for respective of said medical images and said temporal subtraction images, displaying said medical images and said temporal subtraction images superimposed in miniature on respective of said display selection function buttons displayed in said second area of said second screen at least when the respective display selection function button is not activated; and displaying in said first area of said second screen a selected of said medical images and said temporal subtraction images upon activation of a respective display selection function button displayed in said second display area of said second screen.

21. A method as recited in claim 20, comprising:

altering the display of a miniature image in a selected display selection function button displayed in said second display area of said second screen upon activation of the selected display selection function button.

22. A method as recited in claim 14, comprising:

indicating in at least one of said function buttons a diagnostic decision.

23. In a computerized system for displaying medical images, the improvement comprising:

a mechanism configured to obtain a first medical image representative of an anatomy as said anatomy existed at a first point in time;

a mechanism configured to obtain a second medical image representative of the anatomy as said anatomy existed at a second point in time;

a mechanism configured to obtain a temporal subtraction image in which one of said first and second medical images is subtracted from the other thereof;

a mechanism configured to obtain plural diagnostic images of said first and second medical images, each diagnostic image including said one of said first and second medical images having a respective diagnostic annotation, indicative of the results of computer aided diagnosis, superimposed on the respective of said first and second medical images in spatial relation to respective portions of said anatomy;

a mechanism configured to display at least one of said first and second medical images, said temporal subtraction image and said diagnostic images in a first display area of a first display screen; and a mechanism configured to display said first and second medical images, said temporal subtraction image and said diagnostic images including said respective diagnostic annotations in a second display area of said first display screen for visual comparison with the image displayed in said first display area.

24. A system as recited in claim 23, comprising:

a mechanism configured to display said first and second medical images, said temporal subtraction image and said diagnostic images including said respective diagnostic annotations in miniature in said second display area in comparison with a size of the image displayed in said first display area.

25. A system as recited in claim 23, comprising:

a mechanism configured to display said temporal subtraction image grouped with said first and second medical images.

26. A system as recited in claim 23, comprising:

a mechanism configured to display plural of said diagnostic images including said respective diagnostic annotations in miniature in said second display area in comparison with a size of the image displayed in said first display area;

a mechanism configured to display said at least two medical images and said temporal subtraction image in said second display area in miniature in said second display area in comparison with a size of the image displayed in said first display area.

27. A system as recited in claim 26, comprising:
a mechanism configured to display in said second display area said plural of said miniature diagnostic images in association with respective of said miniature at least two medical images.

28. A system as recited in claim 26, comprising:
a mechanism configured to provide in said second display area an all-three display selection function button which when activated results in display of said first and second medical images and temporal subtraction image in said first display area; and
a mechanism configured to display said first and second medical images and temporal subtraction image in said first display area upon activation of said all-three display selection function button.

29. A system as recited in claim 28, comprising:
a mechanism configured to indicate in at least one of said function buttons a diagnostic decision.

30. A system as recited in claim 23, comprising:
a mechanism configured to display in said second display area a respective display selection function button for each diagnostic image, for said first and second medical images, and for said temporal subtraction image such that upon activation of said display selection function button, the respective image corresponding thereto is displayed in said first display area; and
a mechanism configured to display the image corresponding to the activated display selection function button in said first display area upon activation of the respective display selection function button.

31. A system as recited in claim 30, comprising:
a mechanism configured to display said first and second medical images, said temporal subtraction image and said diagnostic images including said respective diagnostic annotations in miniature in said second display area in comparison with a size of the image displayed in said first display area.

32. A system as recited in claim 31, comprising:
a mechanism configured to alter the display of a miniature image superimposed on a selected display selection function button upon activation of the selected display selection function button.

33. A system as recited in claim 32, comprising:
a mechanism configured to indicate in at least one of said function buttons a diagnostic decision.

34. A system as recited in claim 31, comprising:
a mechanism configured to display said first and second medical images and said temporal subtraction image superimposed in miniature on respective of said display selection function buttons at least when the respective display selection function button is not activated.

35. A system as recited in claim 34, comprising:
a mechanism configured to alter the display of a miniature image in a selected display selection function button displayed in said second display area upon activation of the selected display selection function button.

36. A system as recited in claim 30, comprising:
a mechanism configured to provide in said second display area an all-three display selection function button which when activated results in display of said first and second medical images and temporal subtraction image in said first display area; and
a mechanism configured to display said first and second medical images and subtraction image in said first display area upon activation of said all-three display selection function button.

37. A system as recited in claim 30, comprising:
a mechanism configured to display in said second display area an other-images display selection function button which when activated produces a second screen in which plural images of said anatomy are arranged in a matrix, said matrix including a first row in which medical images representative of said anatomy as said anatomy existed at different points in time are arranged, and a second row including at one end of said second row a medical image laterally offset with respect to said medical images of said first row and temporal subtraction images respectively resulting when one of the medical images of the first row and the laterally offset image of said second row is subtracted from the other of the medical images of the first row and the laterally offset image of said second row, each temporal subtraction image being displayed vertically aligned in a column with the respective medical image of the first row from which the respective temporal subtraction image was derived; and
a mechanism configured to display said second screen upon activation of said other-images display selection function button.

38. A system as recited in claim 37, comprising:
said second screen having first and second display areas;
a mechanism configured to display selection function buttons in said second display area of said second screen for respective of said medical images and said temporal subtraction images,
a mechanism configured to display said medical images and said temporal subtraction images superimposed in miniature on respective of said display selection function buttons displayed in said second area of said second screen at least when the respective display selection function button is not activated; and
a mechanism configured to display in said first area of said second screen a selected of said medical images and said temporal subtraction images upon activation of a respective display selection function button displayed in said second display area of said second screen.

39. A system as recited in claim 38, comprising:
a selection mechanism configured to select in said second screen a medical image displayed in said second screen, such that upon activation of said selection mechanism, the selected medical image and associated diagnostic images are displayed in said first screen.

40. A system as recited in claim 39, wherein said selection mechanism comprises:
a change screen display selection function button displayed in said first display area of said second screen and having said selected of said first and second medical images and said temporal subtraction image superimposed thereon, such that upon activation of said change screen display selection function the display mechanism is configured to display said first screen with said selected of said first and second medical images, respective diagnostic images, and said temporal subtraction image displayed in said second display area of said first screen.

41. A system as recited in claim 40, wherein said selection mechanism comprises:
change screen double selection display selection function buttons displayed in said second display area of said second screen and having respective of said medical images and said temporal subtraction images superimposed thereon in miniature, such that upon a double activation of one of said change screen double selection display selection function buttons, the display mechanism is configured to display said first screen with a selected of the medical images corresponding to the double activated change screen double selection display selection function button, and respective diagnostic and temporal subtraction images associated therewith, in said second display area of said first screen.

42. A system as recited in claim 39, wherein said selection mechanism comprises:

change screen double selection display selection function buttons displayed in said second display area of said second screen and having respective of said medical images and said temporal subtraction images superimposed thereon in miniature, such that upon a double activation of one of said change screen double selection display selection function buttons, the display mechanism is configured to display said first screen with a selected medical image corresponding to the double activated change screen double selection display selection function button, and respective diagnostic and temporal subtraction images associated therewith, in said second display area of said first screen.

43. A system as recited in claim 38, comprising:

a mechanism configured to alter the display of a miniature image in a selected display selection function button displayed in said second display area of said second screen upon activation of the selected display selection function button.

44. A system as recited in claim 37, comprising:

a selection mechanism configured to select in said second screen a medical image displayed in said second screen, such that upon activation of said selection mechanism, the selected medical image and associated diagnostic images are displayed in said first screen.

45. A system as recited in claim 30, comprising:

a mechanism configured to indicate in at least one of said function buttons a diagnostic decision.

46. A system as recited in claim 30, comprising:

a mechanism configured to obtain identification information corresponding to said medical image; and a mechanism configured to display said identification information with said medical image.

47. A system as recited in claim 30, comprising:

a mechanism configured to display in said first screen diagnostic result information corresponding to the displayed diagnostic image displayed in said first display area.

48. A computerized system of displaying medical images, comprising:

a mechanism configured to obtain plural medical images representative of an anatomy as said anatomy existed at different points in time;

a mechanism for obtaining at least one temporal subtraction image formed by subtraction of a first of said plural medical images from at least a second of said plural medical images;

a display mechanism configured to display said medical images and said at least one temporal subtraction image arranged in a matrix, said matrix including a first row in which said second medical image is displayed, and a second row in which a temporal subtraction image and said first medical image are displayed with the temporal subtraction image arranged substantially vertically aligned in a column with the second medical image and horizontally aligned with the first medical image in said second row, said subtraction image having been derived by a subtraction operation performed between said first and second medical images.

49. A system as recited in claim 48, wherein said display mechanism is configured to display plural of said medical images in said first row of said matrix and plural temporal subtraction images obtained by subtraction between said first medical image and the medical images of said first row, said temporal subtraction images displayed vertically aligned in respective columns with respective medical images of said first row from which each respective temporal subtraction image was derived and in said row including said first medical image.

50. The system of claim 49, wherein said display mechanism comprises first and second display areas, wherein at least a selected one of said medical images and said temporal subtraction images is displayed in said first display area and said matrix including said medical images and temporal subtraction images is displayed in said second display area in miniature form relative to a size of the selected at least one image displayed in the first display area.

51. A system as in claim 50, wherein said display mechanism is further configured to display a display selection function button in association with each of said medical images and said at least one temporal subtraction image such that upon activation of one of said display selection function buttons, the respective medical image or temporal subtraction image associated therewith is displayed in said first display area.

52. A system as recited in claim 51, comprising:

said display mechanism configured to display said miniature medical images and temporal subtraction images displayed in said second display area superimposed over said display selection function buttons.

53. A system as recited in claim 52, comprising:

said display mechanism configured to alter display of a selected of said medical images and temporal subtraction images superimposed over a respective display selection function button upon activation of the selected display selection function button.

54. The system of claim 48, wherein said display mechanism comprises first and second display areas, wherein at least a selected one of said medical images and said at least one temporal subtraction image is displayed in said first display area and said matrix including said medical images and said at least one temporal subtraction image is displayed in said second display area in miniature form relative to a size of the selected at least one image displayed in the first display area.

* * * * *